United States Patent
Takatani et al.

(10) Patent No.: US 9,592,326 B2
(45) Date of Patent: Mar. 14, 2017

(54) BLOOD PUMP

(71) Applicant: MedTech Heart Inc., Tokyo (JP)

(72) Inventors: Setsuo Takatani, Chiba-ken (JP);
Akihisa Akao, Kanagawa-ken (JP);
Tadahiko Shinzi, Kanagawa-ken (JP)

(73) Assignee: MEDTECH HEART INC., Tokyo (JP)

( * ) Notice: Subject to any disclaimer, the term of this patent is extended or adjusted under 35 U.S.C. 154(b) by 0 days.

(21) Appl. No.: 14/376,573

(22) PCT Filed: Dec. 27, 2012

(86) PCT No.: PCT/JP2012/083881
§ 371 (c)(1),
(2) Date: Oct. 15, 2014

(87) PCT Pub. No.: WO2013/118419
PCT Pub. Date: Aug. 15, 2013

(65) Prior Publication Data
US 2015/0087889 A1    Mar. 26, 2015

(30) Foreign Application Priority Data

Feb. 6, 2012 (JP) .................................. 2012-022626

(51) Int. Cl.
*A61M 1/10* (2006.01)
*F16C 17/02* (2006.01)
(Continued)

(52) U.S. Cl.
CPC .......... *A61M 1/1029* (2014.02); *A61M 1/101* (2013.01); *A61M 1/1015* (2014.02);
(Continued)

(58) Field of Classification Search
None
See application file for complete search history.

(56) References Cited

U.S. PATENT DOCUMENTS 5,779,456 A    7/1998  Bowes et al.
6,234,772 B1*  5/2001  Wampler et al. ........ 417/423.12
(Continued)

FOREIGN PATENT DOCUMENTS

DE       29912577 U1    11/2000
JP       H0296497 U      8/1990
(Continued)

*Primary Examiner* — Erica Lee
(74) *Attorney, Agent, or Firm* — Muncy, Geissler, Olds & Lowe, P.C.

(57) ABSTRACT

A centrifugal blood pump for circulating blood is provided, wherein an impeller makes no contact at all with a housing and a rotating shaft and moves in a rotating manner with the impeller in a stably levitating state. Also provided is a blood pump in which the impeller rotates at high speed even when the blood pump is reduced in scale. The blood pump contains a magnet of enhanced magnetic force at the inside of a housing and at an outer peripheral surface of an impeller and providing a fixed-interval spacing on the periphery of a bearing section makes it possible to ensure a state where no contact at all is made between the housing, a shaft, and the impeller, and makes it possible to cause the impeller to rotate stably over a long period of time.

6 Claims, 5 Drawing Sheets

(51) Int. Cl.
*F04D 13/02* (2006.01)
*F04D 29/08* (2006.01)
*H02K 49/10* (2006.01)
*F16C 32/04* (2006.01)

(52) U.S. Cl.
CPC ......... *A61M 1/1017* (2014.02); *F04D 13/025* (2013.01); *F04D 13/026* (2013.01); *F04D 29/086* (2013.01); *F16C 17/02* (2013.01); *F16C 32/0408* (2013.01); *H02K 49/106* (2013.01)

(56) References Cited

U.S. PATENT DOCUMENTS

| | | | |
|---|---|---|---|
| 2005/0084398 A1* | 4/2005 | Wampler et al. | 417/423.7 |
| 2005/0192525 A1* | 9/2005 | Wieting | A61M 1/3627 604/6.09 |
| 2008/0240947 A1* | 10/2008 | Allaire et al. | 417/420 |
| 2011/0237863 A1* | 9/2011 | Ricci et al. | 600/16 |
| 2012/0035411 A1* | 2/2012 | LaRose et al. | 600/16 |

FOREIGN PATENT DOCUMENTS

| | | |
|---|---|---|
| JP | 2000-240587 | 9/2000 |
| JP | 2005-118237 | 5/2005 |
| JP | 2006-218010 | 8/2006 |
| JP | 2006-226390 | 8/2006 |
| WO | WO 99/53974 | 10/1999 |
| WO | WO 01/42653 A1 | 6/2001 |
| WO | WO 2005/028000 A1 | 3/2005 |

\* cited by examiner

FIG. 6

BLOOD PUMP

TECHNICAL FIELD

The present invention relates to a blood pump. To be specific, the present invention relates to a centrifugal blood pump in which an impeller accommodated in a housing is rotated by magnetic force, thereby circulating blood. The present invention is directed toward an impeller being able to rotate without contacting a housing and a bearing by means of coupling force of magnets disposed inside and outside the housing and dynamic pressure of blood flowing through the housing.

BACKGROUND ART

Extracorporeal blood pumps have hitherto been used during or after surgery (see; for example, Patent Document 1). The blood pump is used as an artificial heart and enables midterm assistance of a cardiac function and treatment of the heart. The blood pump is for circulating blood by centrifugal force, and the centrifugal force is acquired by rotation of an impeller accommodated in a housing. A driven magnet is attached to the impeller accommodated in the housing of the blood pump. The impeller is rotated by rotating a drive magnet disposed outside the housing. In the blood pump disclosed in Patent Document 1, magnets are placed in such a way that magnetic coupling occurs in a direction perpendicular to a ground plane. A bearing is set in a flow path running through a bottom of the housing. The blood pump of Patent Document 1 therefore has contact between the impeller and an interior wall of the housing.

A blood pump described in Patent Document 2 is structured such that an impeller is rotated by magnetic coupling between a drive magnet placed around a rotary shaft and a driven magnet placed on an inner periphery of the impeller. The blood pump of Patent Document 2 additionally has a pair of interacting magnets, one on a housing and the other on an outer periphery of the impeller. The pair of magnets operates to magnetically levitate the impeller and prevent contact between the impeller and the housing.

A blood pump described in Patent Document 3 has a magnet on a sidewall of a housing and another magnet on a circumferential periphery of an impeller and is structured to induce magnetic coupling in a radial direction in which an impeller rotates and to rotate the impeller. The blood pump described in Patent Document 3 assures a blood flow path around a rotating shaft. The impeller can be levitated by means of dynamic pressure of blood flowing through the flow path. The flow path formed around the rotating shaft is a triangular bearing hole positioned around the shaft, and the shaft and a portion of the bearing hole remain in contact with each other.

CITATION LIST

Patent Documents

Patent Document 1: JP 2005-118237 A
Patent Document 2: JP 2006-226390 A
Patent Document 3: JP 2006-218010 A

SUMMARY OF THE INVENTION

Problems to be Solved by the Invention

However, if a contact area, such as a bearing, is present in the blood flow path of the related-art blood pump, there will arise a problem of the contact area inducing a buildup of blood and, in turn, a blood clot and hemolysis. Moreover, a contact area between the housing and the impeller is abraded by rotation of the impeller, which raises a problem of the blood pump not having a long useful life.

Further, in the blood pump structured such that an impeller is magnetically levitated by interaction of magnets, the impeller rotates without contacting the housing. However, the magnetic levitation force is unstable. When the levitation force exerted on the impeller is unstable, the impeller often makes contact with the sidewall of the housing. The thus-contacted area is subject to a problem of rupture of red blood cells and resultant hemolysis. Furthermore, the housing and the impeller must be equipped with magnets for magnetic levitation, which in turn makes the blood pump larger in size.

In the blood pump in which the impeller is levitated by means of dynamic pressure of blood, the blood flow path is laid around the rotating shaft. The flow path is assured by a bearing hole around the shaft. However, the bearing hole is provided while remaining in partial contact with the rotating shaft. Consequently, the blood flowing through the bearing hole builds up to form a blood clot.

For this reason, there is currently sought a blood pump in which an impeller levitates stably within the housing and can rotate without contacting the housing or the rotating shaft. Additionally, a compact blood pump in which the impeller stably levitates within the housing even when a volume of circulating blood is small is also sought so that it can be applied to children and newborns.

Means for Solving the Problems

Accordingly, in order to solve the problems of the related art, the present inventors placed a drive magnet outside the housing and a driven magnet on the impeller inside the housing. Further, magnetic substances are placed on faces of the magnets that are not opposite to each other. Thereby, the present inventors acquired the knowledge that since dispersion of magnetic force is prevented as a result of limitations being imposed on a direction of magnetism of both magnets, the impeller can keep rotating without contacting the housing and the bearing.

The present inventors also created clearance for a blood flow between the impeller and the bearing. Thereby, the present inventors acquired the knowledge that the impeller could stably rotate by means of dynamic pressure of the blood without contacting the housing and the bearing.

The present invention relates to a blood pump having a housing 10, a bearing 20, driven magnets 30, an impeller 40, and a drive magnet 50. The housing 10 has a top surface 2 having an inflow port 1 into which blood flows, a bottom surface 3 positioned opposite the top surface 2, and an outflow port 4 out of which blood is discharged. The bearing 20 is placed while pointing toward the top surface 2 from the bottom surface 3 of the housing 10. The impeller 40 is accommodated in the housing 10 and has the driven magnets 30. The impeller 40 has in its center a through hole for insertion of the bearing 20. The drive magnet 50 is placed outside the housing 10 and rotates along a circumferential periphery 5 of the housing 10. The drive magnet 50 is placed so as to be magnetically coupled with the driven magnets 30 in a radial direction of the impeller 40. Opposed faces are provided on respective sides of the driven magnets 30 and the drive magnet 50 that are opposite to each other, and non-opposed faces are provided on the other sides of the respective opposed faces. The blood pump of the present invention also has magnetic substances 60 and 61. The magnetic substance 60 is placed on the non-opposed face of the drive magnet 50, and the magnetic substance 61 is placed on the non-opposed face of the driven magnets 30. In the blood pump of the present invention, when the drive magnet 50 rotates, the impeller 40 having the driven magnets 30 is rotated. The impeller 40 rotates without contacting the housing 10 and the bearing 20.

The blood pump 100 of the present invention has the magnetic substance 60 on the non-opposed face of the drive magnet 50 and the magnetic substance 61 on the non-opposed faces of the driven magnets 30. The magnetic substances 60 and 61 serve to limit directions of magnetism of the driven magnets 30 and the drive magnet 50 by their magnetism and to prevent dispersion of magnetic force between the driven magnets 30 and the drive magnet 50. To this end, magnetic coupling force between the driven magnets 30 and the drive magnet 50 becomes powerful. In addition, the impeller 40 has a through hole for insertion of the bearing 20. Clearance having a predetermined width is created between the through hole and the bearing 20. Blood flows through narrow clearance between the impeller and the bearing 20, whereby pressure (dynamic pressure) resulting from a liquid flow develops in the clearance.

In the blood pump 100 of the present invention, powerful magnetic coupling force develops between the driven magnets 30 and the drive magnet 50, and dynamic pressure develops in the blood flow path between the impeller 40 and the bearing 20. Consequently, the impeller 40 can rotate without contacting the housing 10 and the bearing 20. In addition, in the blood pump 100 of the present invention, the impeller 40 rotates without contacting the housing 10 and the bearing 20. Therefore, blood does not build up, and a blood clot and hemolysis are less likely to occur. Further, the impeller 40 rotates without making contact, so that abrasion, which would otherwise be caused when the impeller 40 contacts members in the housing 10, can be prevented. As a result, the blood pump 100 can be used over a long period of time.

In the blood pump 100 of the present invention, powerful magnetic coupling force occurs between the driven magnets 30 and the drive magnet 50. Hence, even when the rotating speed of the drive magnet 50 is increased, the driven magnets 30 do not pull out of magnetic coupling. Under normal circumstances, when a volume of blood for filling that flows into a centrifugal blood pump is small, the rotating speed of the impeller 40 needs to be increased. An increase in the rotating speed of the impeller 40, however, may cause great centrifugal force in the impeller 40, as a result of which the driven magnets may pull out of magnetic coupling with the drive magnet. In this regard, the blood pump 100 of the present invention has powerful magnetic coupling force. Therefore, even when the rotating speed of the drive magnet 51 is increased, the driven magnets 30 can be prevented from pulling out of magnetic coupling. Therefore, according to the present invention, since the rotating speed of the impeller 40 can be increased, blood can be stably supplied even when the volume of blood for filling is small. As a consequence, the blood pump 100 can be miniaturized.

In a preferred mode of the present invention, the bearing 20 has the base 21 extending from the bottom surface 3 and the rod-shaped section 22 protruding from the base 21. The base 21 assumes a trapezoidal cylindrical shape that becomes smaller in width toward the rod-shaped section 22. The through hole of the impeller 40 assumes a shape conforming to the rod-shaped section 22 and the base 21 and is formed so as to create clearance of a predetermined width between the rod-shaped section 22 and the base 21.

Like the above configuration, the base 21 is given a trapezoidal cylindrical shape that becomes narrower in width toward the rod-shaped section 22, whereby levitation force stemming from dynamic pressure between the impeller 40 and the bearing 20 can be controlled. As a result, the impeller 40 can rotate more stably within the housing 10.

In a preferred mode of the present invention, the bearing 20 has the base 21 extending from the bottom surface 3 and the rod-shaped section 22 protruding from the base 21. An amount of clearance between the rod-shaped section 22 and the impeller 40 is between or equal to 100 micrometers and 200 micrometers.

The amount of clearance between the rod-shaped section 22 and the impeller 40 is set between or equal to 100 micrometers and 200 micrometers as described in connection with the configuration, whereby the impeller can levitate stably by means of dynamic pressure developing between the impeller 40 and the bearing 20. Consequently, the impeller 40 rotates stably within the housing 10 without making a contact.

In a preferred mode of the present invention, the magnetic substances 60 and 61 are a metal ring including at least one of iron, cobalt, nickel, manganese, and chromium.

The magnetic substances 60 and 61 are formed as a metal ring including at least one of iron, cobalt, nickel, manganese, and chromium as described in connection with the configuration, whereby leakage of magnetic force between the driven magnets 30 and the drive magnet 50 can be efficiently prevented. Thus, magnetic coupling force between the opposed faces of the driven magnets 30 and the drive magnet 50 can be enhanced.

In a preferred mode of the present invention, the trapezoidal cylindrical shape having a smaller width has a slope inclined at an angle of 30 degrees to 60 degrees with respect to the bottom surface 3.

The angle of the slope with respect to the bottom surface 3 is set to 30 degrees to 60 degrees as described in connection with the configuration, thereby making it possible to prevent blood from building up. Further, the slope is set to an angle from 30 degrees to 60 degrees with respect to the bottom surface 3, whereby dynamic pressure developing between the impeller 40 and the bearing 20 can be controlled. Consequently, the impeller 40 can levitate at an appropriate position within the housing 10 and rotate stably within the housing 10.

In a preferred mode of the present invention, the housing 10 includes the top housing 11 and the bottom housing 12, and the top housing 11 and the bottom housing 12 are joined together by the seal structure. The seal structure is a structure in which a protuberance formed on either the top housing 11 or the bottom housing 12 fits into a recess formed in the remaining one of them.

As a result of the seal structure existing between the top housing 11 and the bottom housing 12 as described in connection with the configuration, the top housing 11 and the bottom housing 12 become removably attachable. Moreover, the seal structure is implemented as a structure in which a protuberance formed on either the top housing 11 or the bottom housing 12 fits into a recess formed in the remaining one of them, so that the top housing 11 can be firmly fitted into the bottom housing 12.

Advantages of the Invention

The present invention has the aforementioned matters to define the invention, whereby the impeller 40 can be rotated without contacting the housing 10 and the bearing 20 over a long period of time. Moreover, the present invention has the above-described matters to define the invention, whereby the driven magnet 30 can be prevented from pulling out of magnetic coupling even when the rotating speed of the drive magnet 51 is increased. Therefore, a highly-safe blood pump 100 can be obtained.

Furthermore, the present invention has the foregoing matters to define the invention, whereby the blood pump 100 can be reduced in size and weight. Consequently, according to the present invention, a blood pump 100 operating at a small blood flow and applicable to children and newborns can be obtained.

BRIEF DESCRIPTION OF THE DRAWINGS

FIG. 3(*a*) is an enlarged cross-sectional view of a bearing, and FIG. 3(*b*) is a cross-sectional view taken along line X-X shown in FIG. 3(*a*);

FIG. 5(*a*) is an enlarged cross-sectional view of the bearing, and FIG. 5(*b*) is a cross-sectional view taken along line Y-Y shown in FIG. 5(*a*)

EMBODIMENT FOR CARRYING OUT THE INVENTION

An embodiment for carrying out the present invention will be described hereunder by reference to the drawings. The present invention is not limited to an embodiment to be described below and encompasses modifications conceived by persons skilled in the art by reference to the following embodiment within a self-evident range. Throughout the specification, the expression "A to B" means between or equal to A and B.

(1. Structure of a Blood Pump)

Figure 1:
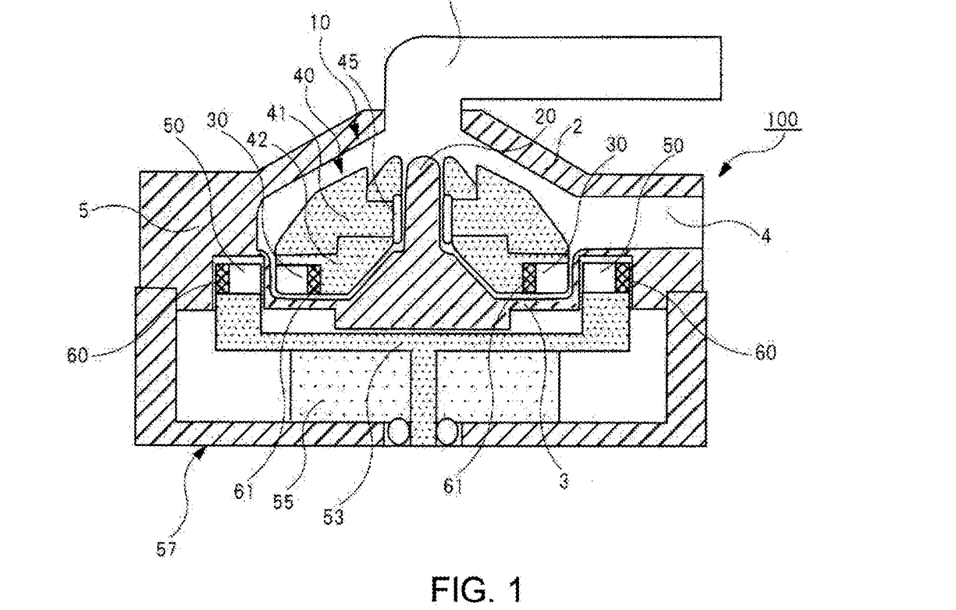
FIG. 1 is a cross-sectional view showing a general configuration of a blood pump.

FIG. 1 is a cross-sectional view showing a general configuration of a blood pump 100 of an embodiment. A housing 10 is made up of a top surface 2, a bottom surface 3 opposite the top surface 2, a circumferential periphery 5 joined to the top surface 2 and the bottom surface 3. The top surface 2 of the housing 10 has an inflow port 1 into which blood flows. The circumferential periphery 5 of the housing has an outflow port 4 out of which blood is discharged. The top surface 2 of the housing 10 can also be inclined toward the inflow port 1 or stand upright with respect to the circumferential periphery 5.

A bearing 20 is placed on the bottom surface 3 of the housing 10 while pointing toward the inside of the housing 10. The bearing 20 is extended along a direction from the bottom surface 3 toward the top surface 2. The direction from the bottom surface 3 toward the top surface 2 corresponds to the vertical direction of FIG. 1. The impeller 40 rotates around the bearing 20 without making contact. The impeller 40 has driven magnets 30, and a drive magnet 50 joined to a motor 55 is placed outside the housing 10. The impeller 40 is rotated by magnetic force developing between the driven magnets 30 and the drive magnet 50.

The inflow part 25 and the outflow port 4 are each joined to the heart of a patient during or after surgery, and the blood pump 100 acts as an artificial heart. The blood flowing into the housing 10 from the inflow port 1 circulates through the inside of the housing 10 by centrifugal force induced by rotary motion of the impeller 40 in the housing 10, being discharged from the outflow port 4.

The impeller 40 is accommodated in the housing 10. The impeller 40 operates to circulate blood within the housing 10 by performing rotary motions within the housing 10. The impeller 40 has in its center a through hole for insertion of the bearing 20. The through hole assumes a shape conforming to the bearing 20 and is formed such that predetermined clearance is created between the bearing 20 and the impeller 40.

The bearing 20 is inserted into the through hole of the impeller 40, and the impeller 40 rotates around the bearing 20 without making contact. The impeller 40 performs rotations while taking a horizontal direction of the housing 10 as a radial direction. It is preferable for the impeller 40 to assume a shape conforming to the geometry of an internal space of the housing 10 so that the blood flowing into the housing 10 can circulate efficiently. The shape of the impeller 40 can be made appropriate in accordance with the volume of blood for filling the housing 10 and a rotating speed of the impeller 40. For example, when an increase in rotating speed of the impeller 40 is desired, irregularities in the impeller 40 can also be made smaller such that resistance the impeller 40 undergoes in a fluid becomes smaller.

The impeller 40 can also be made up of an impeller top 41 and an impeller bottom 42. The impeller top 41 has vanes for circulating blood, and the impeller bottom 42 has the driven magnets 30. In order to enhance magnetic coupling with the drive magnet 50 to be described later, it is preferable for the driven magnet 30 to be mounted on a radial outer periphery of the impeller 40. Although the driven magnets 30 can also be mounted at the radially-outermost periphery of the impeller 40, it is preferable for the driven magnets 30 to be placed on the impeller 40 so as to avoid contact with the blood flowing through the inside of the housing 10. It is preferable to use a material that does not hinder magnetic coupling between the driven magnets 30 and the drive magnet 50 as a material that covers an outer surface of the impeller 40. The driven magnets 30 can also be formed in a ring shape while being continually positioned along the same outer periphery of the impeller bottom 42.

The impeller top 41 has vanes for circulating blood. It is preferable for the vanes of the impeller to be placed at regular intervals from the center to the radial outer periphery of the impeller 40. The number of vanes provided on the impeller top 41 of the present invention is preferably four to twelve and, more preferably, six to eight.

The impeller bottom 42 has the driven magnets 30, and the driven magnets 30 are placed along a radial outer periphery of the impeller 40. Plural driven magnets 30 are placed along the same circumference such that the N pole and the S pole are positioned one after the other. The number of driven magnets 30 is preferably four to twelve and, more preferably, six to eight.

The blood pump 100 of the present invention has a motor 55 placed outside the housing 10 and a motor housing 57 that accommodates the motor 55. A drive magnet mount 53 that performs rotary motion while coupled to the motor 55 is placed within the motor housing 57. The drive magnet mount 53 has the drive magnet 50. The drive magnet mount 53 bears the drive magnet 50 so as to rotationally drive the drive magnet 50 along the circumferential periphery 5 of the housing 10. As shown in, for instance, FIG. 1, it is preferable for the drive magnet mount 53 to have a plane parallel to the bottom surface 3 of the housing 10 and a sidewall extending vertically from the parallel plane in an axial direction. The drive magnet 50 is placed on and secured to the sidewall. The drive magnet mount 53 is provided with such a structure, whereby the drive magnet 50 can be rotated along the circumferential periphery 5 outside the housing 10.

A plurality of N poles and a plurality of S poles are placed to form the drive magnet 50 in such a way that the N poles and the S poles are positioned one after the other along the same circumference. The N poles and S poles making up the drive magnet 50 are each provided preferably in a number of four to twelve and more preferably in a number of six to eight. The drive magnet 50 can also be continually formed in a ring shape along the circumferential periphery 5 outside the housing 10.

The impeller 40 having the driven magnets 30 rotates as a result of rotation of the drive magnet 50 mounted on the drive magnet mount 53. The driven magnets 30 and the drive magnet 50 are placed so as to be magnetically coupled together in the radial direction of the impeller 40 by way of the circumferential periphery 5 of the housing 10. The impeller 40 levitates within the housing 10 by means of pressure (motive energy) of the blood flowing through the inside of the housing to be described later, and can accordingly rotate without contacting the housing 10 and the bearing 20.

The drive magnet 50 of the blood pump 100 of the present invention is placed on the sidewall of the drive magnet mount 53. The driven magnets 30 and the drive magnet 50 are positioned so as to be magnetically coupled together in the radial direction of the impeller 40 by way of the circumferential periphery 5 of the housing 10. Since the drive magnet 50 is mounted on the drive magnet mount 53, the location where the drive magnet is positioned can be freely changed by adjusting the shape of the drive magnet mount 53. For instance, when the driven magnets 30 are placed on an upper side of the impeller 40 in its vertical direction, the drive magnet 50 can be placed high in the axial direction by increasing the height of the sidewall of the drive magnet mount 53. As described above, the position and layout of the drive magnet 50 can be adjusted by changing the shape of the drive magnet mount 53.

It is preferable to use a permanent magnet made from a rare-earth magnet for the drive magnet 50 and the driven magnets 30. The rare-earth magnet possesses a high magnetic property and hence can enhance magnetic coupling between the driven magnets 30 and the drive magnet 50. As a result, the impeller 40 can be rotated at high speed. In addition, use of the permanent magnet made from a rare-earth magnet enables stable use of the blood pump over a long period of time.

The rotating speed of the impeller 40 can be freely controlled by enhancing magnetic coupling force between the driven magnets 30 and the drive magnet 50. So long as the magnetic coupling force between the driven magnets 30 and the drive magnet 50 is powerful, the driven magnets 30 can rotate in agreement with the rotating speed of the drive magnet 50 without pulling out of magnetic coupling even when the rotating speed of the drive magnet 50 is increased. Moreover, so long as the magnetic coupling force between the driven magnets 30 and the drive magnet 50 is powerful, even when the rotating speed of the drive magnet 50 is decelerated, the rotating speed of the driven magnets 30 can be quickly synchronized with the rotating speed of the drive magnet 50. As described above, since the rotating speed of the driven magnets 30 can be freely controlled, the volume of blood discharged from the blood pump 100 can be controlled in accordance with a patient's state.

(2. Blood Flow Path)

Figure 2:
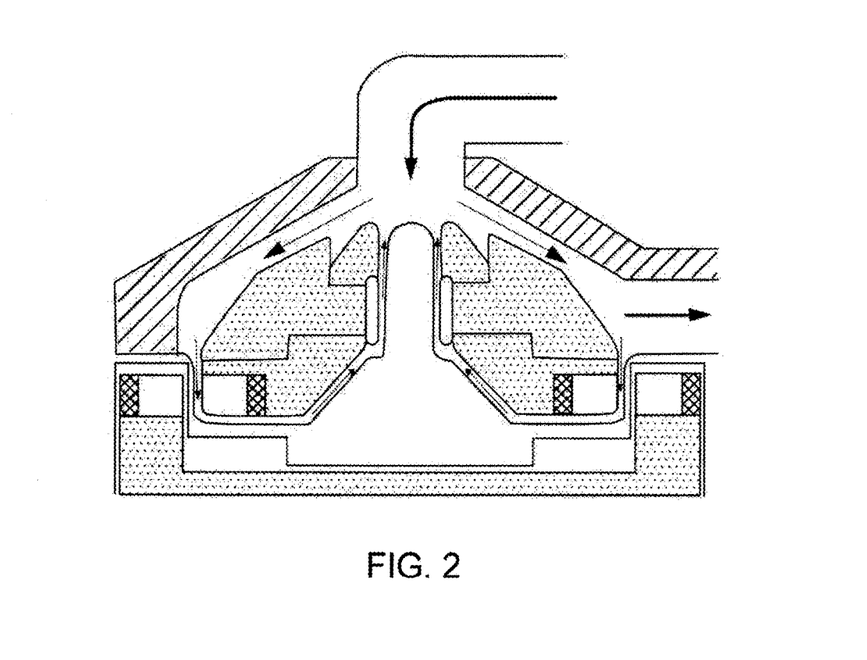
FIG. 2 is a schematic showing a blood flow in the blood pump.

FIG. 2 is a schematic showing a flow of blood within the housing 10. The blood flowing into the housing 10 from the inflow port 1 is circulated through a blood flow path in the housing 10 by means of centrifugal force stemming from torque of the impeller 40, being discharged from the outflow port 4.

In the blood pump 100 of the present invention, the driven magnets 30 and the drive magnet 50 are magnetically coupled. Therefore, the drive magnet 50 is rotated by driving force of the motor 55, whereby the driven magnets 30 are rotated. The impeller 40 having the driven magnets 30 rotates concomitantly. By rotary motion of the impeller 40, the blood can circulate within the housing 10.

A portion of blood flowed into the housing 10 from the inflow port 1 flows downwards relative to the impeller 40 by way of clearance between the housing 10 and the impeller 40 without being discharged from the outflow port 4. This portion of blood passes through clearance between the impeller 40 and the circumferential periphery 5 of the housing 10, flowing through clearance between the impeller 40 and the bottom surface 3 of the housing 10. The blood flowing into the clearance between the impeller 40 and the bottom surface 3 of the housing 10 subsequently reaches a space between the impeller 40 and the inflow port 1 by passing through narrow clearance between the bearing 20 and the impeller 40, merging with blood newly flowing from the inflow port 1. Most of the merged blood flows out of the outflow port 4, but a portion of the blood again circulates within the housing 10.

In the blood pump 100 of the present invention, blood flows through narrow clearance between the bearing 20 and the impeller 40. Blood flows into the narrow clearance between the bearing 20 and the impeller 40, whereby dynamic pressure arises between the bearing 20 and the impeller 40. The dynamic pressure acts so as to prevent the impeller 40 from contacting the bearing 20. Consequently, the impeller 40 can rotate without contacting the housing 10 and the bearing 20.

Since the impeller 40 rotates without contacting the housing 10 and the bearing 20, blood does not build up in the blood flow path, so that occurrence of a blood clot and hemolysis can be prevented. Moreover, the impeller 40 rotates without making contact, so that abrasion of members in the housing 10, which would otherwise occur, can be prevented. The blood pump can therefore be used over a long period of time.

A preferable structure for the blood flow path is to prevent a buildup of blood. Blood components are likely to build up in an area where a great change occurs in a flow direction of blood or a recess in the flow path. A blood clot may occur in this area. Therefore, it is preferable to prevent occurrence of an abrupt change in the flow direction of blood or formation of an angular area in a flow path at a bifurcation in a direction in which blood is to flow.

(3. Magnetic Substance)

Figure 3:
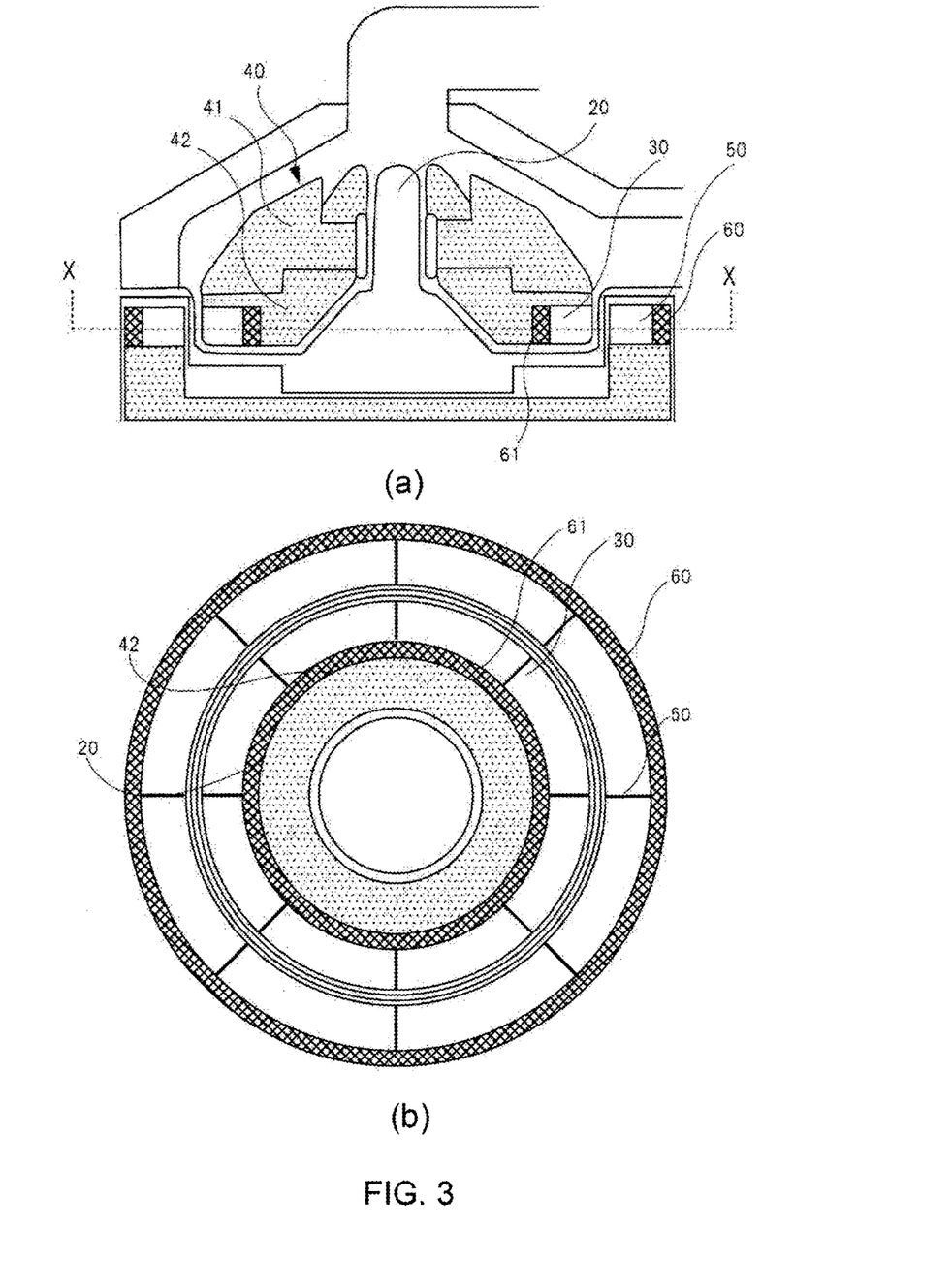

FIG. 3(a) is an enlarged cross-sectional view of the bearing 20. FIG. 3(b) is a cross-sectional view taken along line X-X shown in FIG. 3(a). As shown in FIG. 3, the blood pump of the present invention has magnetic substances 60 and 61 on respective faces of the driven magnets 30 and the drive magnet 50 that are not opposite to each other. The driven magnets 30 and the drive magnet 50 of the blood pump of the present invention are positioned so as to be magnetically coupled to each other by way of the circumferential periphery 5 of the housing 10 in the radial direction of the impeller 40. Aside of the driven magnets 30 and a side of the drive magnet 50 that are to be magnetically coupled to each other are referred to as mutually-opposed faces. Faces on the other sides of the respective magnets are referred to as non-opposed faces. The driven magnets 30 and the drive magnet 50 each have an opposed face and a non-opposed face. The magnetic substance 60 is disposed on the non-opposed face of the drive magnet 50. The magnetic substance 61 is disposed on the non-opposed face of the driven magnet 30. It is preferable for the magnetic substance 60 to be placed on the non-opposed face of the drive magnet 50, and it is preferable for the magnetic substance 61 to be placed on the non-opposed faces of the driven magnets 30. The magnetic substance 60 and the magnetic substance 61 can also be placed in contact with or separated from the non-opposed faces of the drive magnet 50 and the driven magnets 30 with space therebetween. It is also preferable for the magnetic substance 60 and the magnetic substance 61 to be placed in a ring shape on the non-opposed faces of the driven magnets 30 and the non-opposed face of the drive magnet 50.

The magnetic substances 60 and 61 prevent leakage of a magnetic field to the non-opposed faces of the drive magnet 50 and the driven magnet 30. The magnetic substances 60 and 61 prevent leakage of the magnetic field originating in the non-opposed faces of the drive magnet 50 and the driven magnets 30, thereby making it possible to enhance magnetic coupling between the opposed-faces of the driven magnets 30 and the drive magnet 50. The magnetic coupling force achieved when the magnetic substances 60 and 61 are placed on the non-opposed surfaces of the drive magnet 50 and the driven magnets 30 becomes about 1.3 to 3 times greater than the magnetic coupling force achieved when the magnetic substances 60 and 61 are not placed.

The magnetic substances are preferably a metal ring containing at least one of iron, cobalt, nickel, manganese, and chromium and, particularly preferably, an iron ring. The metal ring refers to a ring-shaped metal body contiguously placed on each of the non-opposed faces of the driven magnets 30 and the drive magnet 50. In order to prevent leakage of the magnetic field from the respective non-opposed faces of the driven magnet 30 and the drive magnet 50, it is preferable to contiguously place the magnetic substance on each of the non-opposed faces of the driven magnets 30 and the drive magnet 50. Since the blood pump 100 of the present invention has the powerful magnetic coupling force between the driven magnets 30 and the drive magnet 50, the driven magnets 30 can be prevented from pulling out of magnetic coupling even when the rotating speed of the drive magnet 50 is increased. Therefore, the impeller 40 of the blood pump 100 of the present invention can rotate at high speed.

In order to obtain a blood pump applicable to children and newborns, the volume of blood for filling that flows into the blood pump must be reduced. When the volume of blood for filling that flows into a centrifugal blood pump is reduced, the rotating speed of the impeller 40 must be increased to circulate blood. In the blood pump of the present invention, the driven magnets 30 are less likely to pull out of magnetic coupling even when the rotating speed of the drive magnet 51 is increased. Accordingly, the driven magnets 30 can rotate in agreement with the rotating speed of the drive magnet 50. Since the impeller 40 having the driven magnets 30 can rotate at high speed as described above, the blood pump 100 can consequently be miniaturized.

The volume of blood for filling the housing 10 of the blood pump 100 of the present invention can be set to a value of 5 cc or less and can also be used for children and newborns to whom the related-art blood pumps are rarely applied. The blood pump 100 of the present invention can also be used as a blood pump for adults by adjusting the structure and size of the housing 10 and the impeller 40.

The rotating speed of the impeller 40 can be freely controlled by intensifying the magnetic coupling force between the driven magnets 30 and the drive magnet 50 by use of the magnetic substances 60 and 61. So long as the magnetic coupling force between the driven magnets 30 and the drive magnet 50 is powerful, the rotating speed of the driven magnets 30 can be quickly synchronized with the rotating speed of the drive magnet 50. Since the rotating speed of the driven magnets 30 can be freely adjusted as described above, the volume of blood discharged to the blood pump 100 can be controlled in accordance with the patient's state.

The blood pump of the present invention has the magnetic substance 60 placed on the non-opposed face of the drive magnet 50 along the circumferential periphery outside the housing. Consequently, the structure makes the magnetic field of the drive magnet 50 less easy to leak out of the blood pump 100. When the magnetic force of the drive magnet 50 is powerful and has leaked out of the blood pump, medical and electrical equipment disposed around the blood pump would be adversely affected, which may raise a problem. However, the magnetic substance 60 provided on the non-opposed face of the drive magnet 50 can shield the magnetic force of the drive magnet 50 within the blood pump 100. Hence, the blood pump can be used without paying consideration to surrounding environments.

(4. Shape of Bearing)

Figure 4:
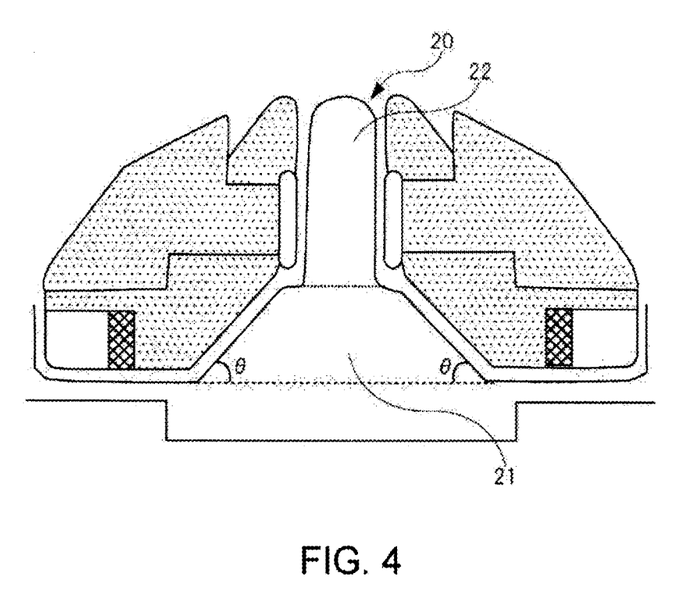
FIG. 4 is an enlarged cross-sectional view of the bearing of the blood pump.

FIG. 4 is an enlarged cross-sectional view of the bearing 20 of the blood pump 100. The bearing 20 of the blood pump 100 of the present invention has a base 21 extending from the bottom surface 3 and a rod-shaped section 22 protruding from the base 21. The base 21 assumes a trapezoidal cylindrical shape which has a smaller width toward the rod-shaped section 22. As shown in FIG. 4, a cross section of the base 21 can also assume a trapezoidal shape. The height of the base 21 is 10% to 50%, preferably 20% to 40%, and more preferably 25% to 35%, relative to an axial height of the bearing 20. The height of the base 21 is set to 10% to 50% relative to the axial height of the bearing 20, whereby the dynamic pressure developing between the impeller 40 and the bearing 20 can be controlled to an appropriate range.

The impeller 40 has a through hole, and the through hole is formed so as to conform to the shape of the rod-shaped section 22 and the base 21, and create clearance of a predetermined width between the rod-shaped section 22 and the base 21.

The trapezoidal cylindrical shape by means of which the base 21 becomes smaller toward the rod-shaped section 22 has a slope inclined with respect to the bottom surface 3. An angle of the slope with respect to the bottom surface 3 is denoted by $\theta$ in FIG. 4. It is desirable that $\theta$ be made by an angle of 30 to 60 degrees and more preferably an angle of 40 to 50 degrees. The slope is made at an angle of 30 to 60 degrees with respect to the bottom surface 3, whereby a flow direction of blood becomes unchanged in the vertical direction. Since the flow direction of blood gradually changes stepwise, the blood flow does not build up in the blood flow path, so that blood circulates efficiently.

Force for levitating the impeller, which originates from the dynamic pressure between the impeller 40 and the bearing 20, can be adjusted by providing the base 21 with a trapezoidal cylindrical shape that becomes smaller toward the rod-shaped section 22.

Blood flows between the impeller 40 and the rod-shaped section 22, whereby dynamic pressure develops between the impeller 40 and the rod-shaped section 22. The dynamic pressure makes it possible for the impeller 40 to levitate within the housing without contacting the bearing 20. However, if the dynamic pressure between the impeller 40 and the rod-shaped section 22 is too powerful or weak, the impeller 40 cannot levitate at an appropriate position within the housing 10.

The blood flow path lying between the impeller 40 and the base 21 is made at an inclination with respect to the axial direction. Therefore, the direction of dynamic pressure acting on the impeller 40 is changed, so that the levitation force of the impeller 40 can be controlled to an optimum magnitude.

It is preferable that the dynamic pressure developing between the impeller 40 and the rod-shaped section 22 should be controlled within an appropriate range in order for the impeller 40 to stay out of contact with the bearing 20. Therefore, the dynamic pressure developing between the impeller 40 and the bearing 20 can be set to an optimum magnitude by controlling the length of the flow path lying between the impeller 40 and the rod-shaped section 22 and the length of the flow path lying between the impeller 40 and the base 21.

FIG. 5(a) is an enlarged cross-sectional view of the bearing 20. FIG. 5(b) is a cross-sectional view taken along line Y-Y shown in FIG. 5(a). In FIG. 5(b), clearance between the rod-shaped section 22 and the impeller 40 is denoted by A. In the blood pump of the present invention, an amount of clearance A is between or equal to 50 micrometers and 500 micrometers, preferably between or equal to 100 micrometers and 350 micrometers, and more preferably between and equal to 100 micrometers and 200 micrometers. If the amount of clearance between the rod-shaped section 22 and the impeller 40 is too short, blood will build up or hemolysis will occur. Meanwhile, if the amount of clearance between the rod-shaped section 22 and the impeller 40 is too large, the dynamic pressure developing between the rod-shaped section 22 and the impeller 40 will become smaller, so that the impeller 40 cannot levitate stably within the housing 10. Moreover, if the amount of clearance between the rod-shaped section 22 and the impeller 40 is too wide the impeller 40 will cause horizontal wobbling or tilts. Thus, rotation of the impeller 40 cannot be made stable. It is preferable for the amount of clearance A between the rod-shaped section 22 and the impeller 40 to be set in such a way that blood does not build up and that the dynamic pressure developing between the rod-shaped section 22 and the impeller 40 reaches an appropriate magnitude.

The amount of clearance between the base 21 and the impeller 40 is between or equal to 50 micrometers and 1500 micrometers, preferably between or equal to 100 micrometers and 1000 micrometers, and more preferably between or equal to 300 micrometers and 800 micrometers. It is preferable for the amount of clearance between the base 21 and the impeller 40 to be greater than the amount of clearance between the rod-shaped section 22 and the impeller 40.

Figure 5:
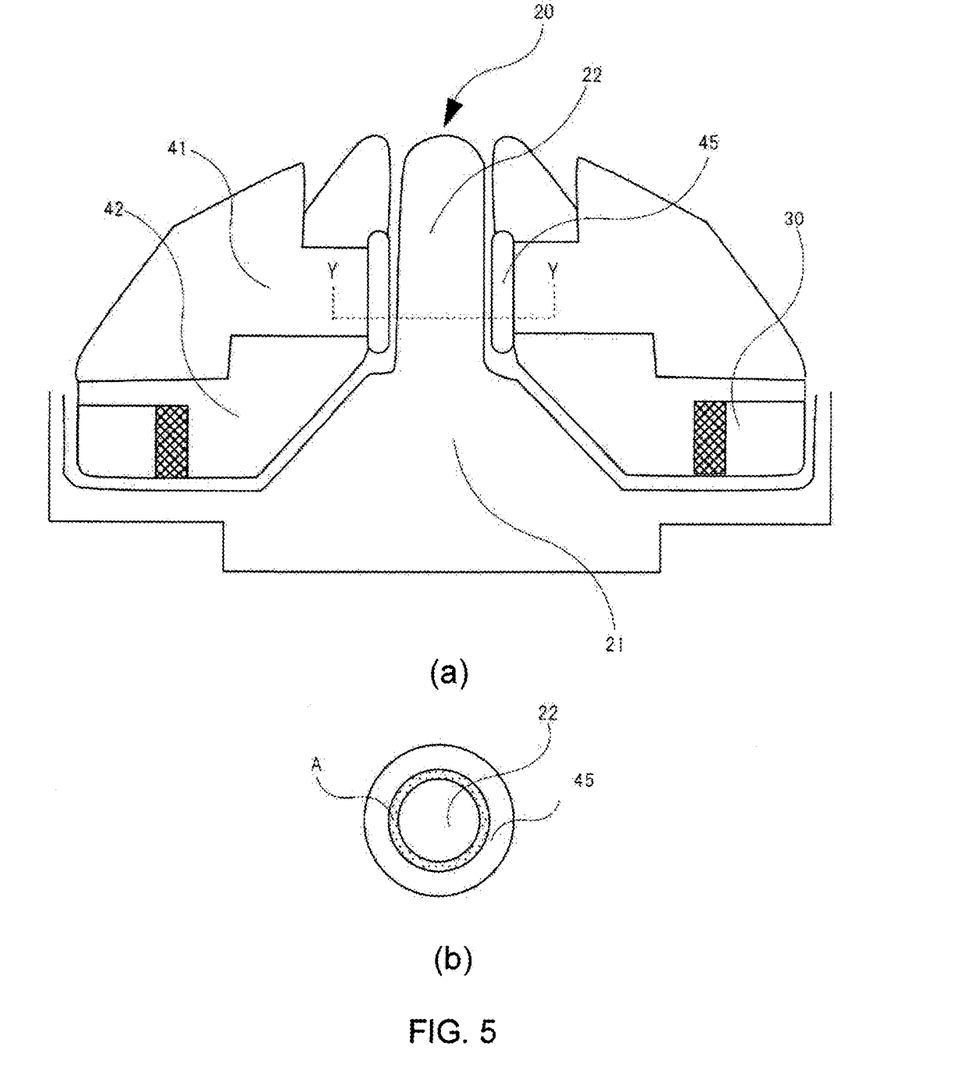

As shown in FIG. 5, the impeller 40 can also have a shaft joint 45. The shaft joint 45 is provided to lessen frictional resistance between the rod-shaped section 22 and the impeller 40. It is preferable that the shaft joint 45 should be made from a material which exhibits low frictional resistance between the bearing 20 and the rod-shaped section 22 and which differs from the material used for molding the rod-shaped section 22. For instance, a material made from polyethylene can be used for the shaft joint 45.

The rotating speed of the impeller 40 can be increased by reducing frictional resistance between the rod-shaped section 22 of the bearing 20 and the shaft joint 45. Further, the blood pump 100 can be used over a long period of time.

Figure 6:
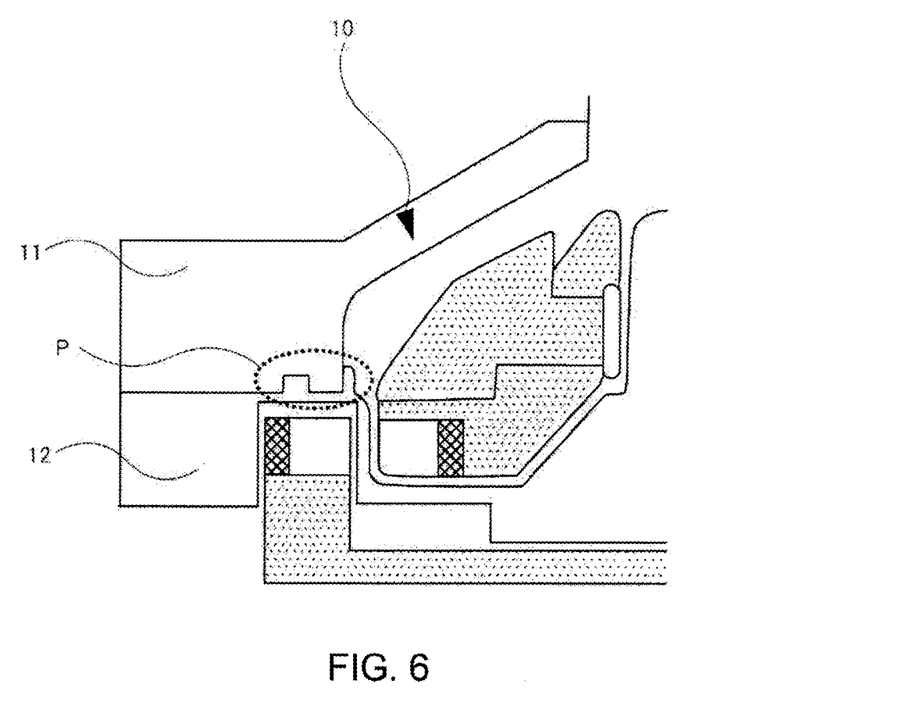
FIG. 6 is an enlarged view showing a configuration outline of a seal structure between a top housing and a bottom housing.

FIG. 6 is an enlarged view showing a structural outline of a seal structure between a top housing and a bottom housing. The housing 10 of the present invention can also have a structure including a top housing 11 and a bottom housing 12. The housing 10 is made up of a member that enables removal attachment of the top housing 11 and the bottom housing 12, thereby making it easy to perform adjustment and maintenance of the member accommodated in the housing.

When the housing 10 assumes a structure made up of the top housing 11 and the bottom housing 12, the top housing 11 and the bottom housing 12 are joined together by means of a seal structure. In FIG. 6, the seal structure is denoted by an area P enclosed by circular dotted lines. As shown in FIG. 6, the seal structure P is a structure in which a protuberance formed on either the top housing 11 or the bottom housing 12 fits into a recess formed in a remaining one of them. The seal structure is formed by the protuberance fitting into the recess, whereby the fit between the top housing 11 and the bottom housing 12 becomes sturdy. As a result of formation of the seal structure, the top housing 11 and the bottom housing 12 are fitted without clearance, so that leakage of blood can be prevented.

It is preferable for the bottom housing 12 of the housing 10 of the present invention to have two protuberances. It is preferable for one of the two protuberances to be formed more inside the housing when compared with the top housing 11. It is preferable that the protuberance formed more inside the housing when compared with the top housing 11 should be narrower in width than the other protuberance.

It is preferable for the top housing 11 of the housing 10 of the present invention to have one recess. One protuberance of the bottom housing 12 fits into the recess, and the other protuberance of the bottom housing 12 is formed more inside the housing when compared with the top housing 11.

By means of engagement of the two protrusions formed in the bottom housing 12 with one recess formed in the top housing 11, the housing 10 of the present invention allows a firm fit between the top housing 11 and the bottom housing 12 while enabling removal and attachment of the top housing 11 with respect to the bottom housing 12.

A lubricant may also be applied to the fit between the recess and the protrusion of the seal structure of the present invention. Moreover, in order to enhance sealing performance, an elastic sealant can also be bonded to an interface between the recess and the protrusion of the seal structure.

The impeller 40 of the present invention can rotate without contacting the housing 10 and the bearing 20 by means of the powerful magnetic coupling force between the driven magnets 30 and the drive magnet 50 and the dynamic pressure of the blood flowing through clearance between the housing 10 and the bearing 20. In the blood pump 100 of the present invention, the impeller 40 rotates without contacting the housing 10 and the bearing 20, and hence blood does not build up, and occurrence of a blood clot or hemolysis is prevented. Moreover, in the blood pump 100 of the present invention, since the impeller 40 rotates without contacting the housing 10 and the bearing 20, occurrence of abrasion, which would otherwise be caused contacts with individual members in the housing g10, does not occur. The blood pump 100 of the present invention can thereby be continually used for a long period of time, for instance, for over one year or more.

The blood pump 100 of the present invention has the powerful magnetic coupling force between the driven magnet 30 and the drive magnet 50. Therefore, the driven magnets 30 can be prevented from pulling out of magnetic coupling even when the rotating speed of the drive magnet 50 is increased. Since the blood pump 100 of the present invention does not pull out of magnetic coupling even when the rotating speed of the drive magnet 51 is increased, the rotating speed of the impeller 40 can be increased. As a result, the blood pump 100 can be miniaturized. Consequently, the blood pump 100 of the present invention can also be used as a blood pump for children and newborns to which the related-art blood pumps have rarely been applied.

Moreover, the blood pump 100 of the present invention uses dynamic pressure in order to levitate the impeller 40 within the housing 10. Therefore, there is no necessity to provide magnets other than the driven magnets 30 and the drive magnet 50 used for rotating the impeller 40, so that the blood pump can be reduced in size and weight.

INDUSTRIAL APPLICABILITY

The present invention can be utilized in the field of medical equipment.

DESCRIPTION OF REFERENCE NUMERALS

1 INFLOW PORT
2 TOP SURFACE
3 BOTTOM SURFACE
4 OUTFLOW PORT
5 CIRCUMFERENTIAL PERIPHERY
10 HOUSING
11 TOP HOUSING
12 BOTTOM HOUSING
20 BEARING
21 BASE
22 ROD-SHAPED SECTION
30 DRIVEN MAGNET
40 IMPELLER
41 IMPELLER TOP
42 IMPELLER BOTTOM
45 SHAFT JOINT
50 DRIVE MAGNET
53 DRIVE MAGNET MOUNT
55 MOTOR
57 MOTOR HOUSING
60 MAGNETIC SUBSTANCE
61 MAGNETIC SUBSTANCE
100 BLOOD PUMP
P SEAL STRUCTURE

The invention claimed is:

1. A blood pump comprising:
a housing that includes a top surface having an inflow port into which blood flows, a bottom surface placed opposite the top surface, and a circumferential periphery joined to the top surface and the bottom surface and having an outflow port from which blood is discharged;
a bearing placed within the housing, and comprising a longitudinal axis extending from the bottom surface toward the top surface of the housing;
an impeller accommodated in the housing comprising a center axis extending from the top surface to the bottom surface of the housing and having driven magnets positioned radially outward from the center axis and spaced around a circumferential periphery of the impeller, the center of the impeller comprising a through hole along the center axis for insertion of the bearing;
drive magnets that are placed radially outward from the driven magnets and outside the housing so as to be magnetically coupled with the driven magnets in a radial direction of the impeller; and
a motor configured to rotate the drive magnets, wherein when the drive magnets are rotated, they cause the driven magnets to rotate the impeller; wherein
each of the driven magnets comprise a face that opposes a face of the respective drive magnet and taken as opposing faces, and each driven magnet and each drive magnet having a face on the opposite side of the opposing faces and taken as non-opposing faces, and magnetic substances are placed on the non-opposed faces of the drive magnets and the magnetic substances are placed on the non-opposed faces of the driven magnets; and
the impeller rotates without contacting the housing and the bearing when the drive magnets rotates by the motor, wherein
the bearing comprises a base positioned adjacent the bottom surface and a rod-shaped section protruding from the base toward the top surface;
the base comprising a trapezoidal cylindrical shape that becomes narrower in width toward the rod-shaped section: and
the through hole of the impeller comprises a dimension so as to create predetermined clearance between the impeller and the bearing along the shape of the base and the rod-shaped section.

2. The blood pump according to claim 1, wherein the clearance between the rod-shaped section and the impeller has a width between or equal to 100 micrometers and 200 micrometers.

3. The blood pump according to claim 1, wherein the magnetic substances are a metal ring including at least one of iron, cobalt, nickel, manganese, and chromium.

4. The blood pump according to claim 1, wherein the trapezoidal cylindrical shape has a slope inclined at between 30 degrees and 60 degrees with respect to the bottom surface.

5. The blood pump according to claim 1, wherein the housing comprises the bottom housing joined to the top housing by a seal structure, and
the seal structure is a structure in which a protuberance formed on either the top housing or the bottom housing fits into a recess formed in a remaining one of the top housing and the bottom housing.

6. The blood pump according to claim 1, wherein the drive magnets and the driven magnets are permanent magnets.

* * * * *